United States Patent [19]

Itoh et al.

[11] Patent Number: 4,686,191
[45] Date of Patent: Aug. 11, 1987

[54] RECOMBINANT PLASMID CONTAINING HUMAN INTERFERON-BETA GENE

[75] Inventors: Seiga Itoh, Sagamihara; Tatsunari Nishi, Machida; Tamio Mizukami, Machida; Tadashi Matsumoto, Machida; Tetsuo Oka, Yokohama; Tadatsugu Taniguchi; Haruo Sugano, both of Tokyo, all of Japan

[73] Assignees: Hakko Kogyo Co., Ltd. Kyowa; Juridical Foundation, Japanese Foundation for Cancer Research, both of Tokyo, Japan

[21] Appl. No.: 452,290

[22] Filed: Dec. 22, 1982

[30] Foreign Application Priority Data

Dec. 25, 1981 [JP] Japan ................. 56-21393

[51] Int. Cl.$^4$ .............. C12N 1/00; C12N 15/00; C12N 1/20; C12P 21/00; C12P 21/06; C12P 21/02; C12P 21/04; C12P 19/34; C07H 21/04
[52] U.S. Cl. ................... 435/320; 435/60; 435/69; 435/70; 435/71; 435/91; 435/172.3; 435/253; 536/27
[58] Field of Search .......... 435/68, 70, 91, 172.3, 435/253, 317, 71, 69; 536/27

[56] References Cited

U.S. PATENT DOCUMENTS 4,349,629  9/1982  Carey et al. ............. 435/172.3

FOREIGN PATENT DOCUMENTS 0041313  9/1981  European Pat. Off. ......... 435/172.3
0048970  7/1982  European Pat. Off. ......... 435/172.3

OTHER PUBLICATIONS

Taniguchi et al.: Gene 10, 11 (1980).
Taniguchi et al.: Proc. Natl. Acad. Sci., USA 77, 5230 (1980).
Tacon et al.: Molec. gen. Genet. 177, 427 (1980).
Emtage et al.: Nature 283, 171 (1980).
Hallewell et al.: Gene 9, 27 (1980).
Goeddel et al.: Nature 281, 544 (1979).
Edman et al.: Nature 291, 503 (1981).
Young et al.: Cell 17, 225 (1979).
M. Houghton, et al., Proc. Battelle Conf. Genet. Eng. 1981 5, 51–57 (Eng.).
M. Houghton, Chemical Abstracts, vol. 97, No. 7, (1982), p. 168, No. 50595W, "The Cloning and Expression of a Human Fibroblast Interferon Gene in Bacteria".
H. Shepard et al., Chemical Abstracts, vol. 96, No. 21 (1982), p. 174, No. 175316s, "Increased Synthesis in E. Coli of Fibroblast and Leukocyte Interferons through Alterations in Ribosome Bindiny Sites".
J. D. Windass, et al., Nucleic Acids Research, vol. 10, No. 21, (1982), pp. 6639–6657, "The Construction of a Synthetic Escherichia Coli Trp promoter and its use in the Expression of a Synthetic Interferon Gene".
D. V. Goeddell, et al., Nucleic Acids Research, vol. 8, No. 18, (1980), pp. 4057–4074, "Synthesis of Human Fibroblast Interferon by E. Coli".
G. F. Miozzari, et al., J. Bact., vol. 133, No. 3, (1978), pp. 1457–1466, "Translation of the Leader region of the Escherichia Coli Tryptophan Operon".
G. N. Bennett, et al., Mol. Biol., vol. 121, (1978), pp. 113–137, "Nucleotide Sequence of the promoter–Operator Region of the Tryptophan Operon of Escherichia Coli".
F. Lee, et al., J. Mol. Biol., vol. 121, (1978), pp. 193–217, "Comparison of the Nucleotide Sequences of the Initial Transcribed Regions of the Tryptophan Operons of Escherichia Coli and Salmonella Typhimurium".

Primary Examiner—James Martinell, Ph.D.
Attorney, Agent, or Firm—Fitzpatrick, Cella, Harper & Scinto

[57] ABSTRACT

Recombinant vector plasmids containing a DNA fragment coding for human interferon-$\beta$ inserted downstream from a tryptophan promoter are useful for transformation of microorganisms such as Escherichia coli which transformants produce human interferon-$\beta$.

1 Claim, 13 Drawing Figures pKYP-1 (9.2Kb)

pKYP-5 (5.4Kb)

pKYP-12

CLONING OF THE trp OPERON FROM THE λPtrp

CLONING OF PLASMID DNAs IN A VECTOR

RECOMBINANT PLASMID CONTAINING HUMAN INTERFERON-BETA GENE

BACKGROUND OF THE INVENTION

The present invention relates generally to recombinant plasmids and, more specifically, to recombinant plasmids containing a DNA coding for human interferon-β (referred to as IFN-β hereinafter) and a process for producing IFN-β.

Expression of genes in organisms is achieved through a series of biological reactions involving synthesis of an RNA using a DNA as a template, i.e. the transcription step and synthesis of a polypeptide based on the information of mRNA, i.e. the translation step. Such recombinant DNA technology has now been developed to the extent that its industrial application has become possible.

In this connection, it is important to develop a method for the insertion of foreign genes into a plasmid vector for the efficient synthesis of the polypeptide coded by the foreign gene in a microorganism.

For the efficient expression of foreign genes in a microorganism, particularly in *Escherichia coli*, various attempts have heretofor been made. In order to increase the rate of transcription, lactose operon promoter, tryptophan operon promoter and the like have been employed as a promoter, i.e. the initiation site for transcription with RNA polymerase. In order to increase the rate of translation, various recombinants wherein the length between the Shine-Dalgarno sequence (referred to as SD sequence hereinafter) and the initiation site of the translation is varied, generally 3 to 15 base pairs, have been prepared. See Keiichi Itakura, Science 198, 1056–1063 (1977); A. H. Seeburg et al.: Nature 276, 795–798 (1978) and J. A. Martial et al.: Science 205, 602–607 (1979). As a practical problem, however, with use of the examples mentioned above, proteins are generally produced as fused proteins consisting of two or more proteins. Although the direct production of intact proteins has been reported by David V. Goeddel et al.: Nature, 281, 544–548 (1979); Goeddel et al.: Nature, 287, 411–416 (1980) and Goeddel et al.: Nucleic Acid Research, 8, 4057–4074 (1980), the method of direct production is inconvenient because a special synthetic DNA is used as a joint to insert the foreign gene together with the initiation codon ATG for translation downstream from the promotor. Thus, a need exists for an efficient and industrially applicable method for synthesis of a polypeptide coded by a foreign gene in a microorganism. To this end, vectors have now been constructed which overcome the deficiencies of the known plasmid vectors and which are useful particularly for efficient expression of IFN-β in *Escherichia coli*.

SUMMARY OF THE INVENTION

In accordance with the present invention, plasmid vectors are constructed which have a ClaI site and a HindIII site downstream from the *Escherichia coli* tryptophan promoter (referred to as trp promoter hereinafter) and the SD sequence of tryptophan leader peptide, derived from *Escherichia coli* transducing phage, λcI857trpED10. By using the two restriction sites (ClaI and HindIII) instead of a synthetic DNA as a joint, many recombinants are readily constructed wherein the length between the SD sequence and the initiation site for translation of IFN-β is varied. As a result, IFN-β is efficiently produced by culturing an *Escherichia coli* strain transformed with the recombinant.

Several plasmid vectors having *Escherichia coli* trp promoters have been reported, e.g., Norman H. Carey: Japanese Published Unexamined Patent Application No. 36500/81; R. A. Hallewell et al.: Gene 9, 27–47 (1980); Emtage et al.: Nature, 283, 171–174 (1980) and J. C. Edman et al.: Nature, 291, 503–506 (1981). The plasmid vectors of the present invention on the other hand have the unique characteristic of having two or more cleavage sites for restriction endonucleases selected from ClaI, HindIII, EcoRI, BamHI, PstI and the like immediately after, about the length of 0 to 20 base pairs, the SD sequence and the efficiency of translation can be increased by adjusting the length between the SD sequence and the initiation site of the foreign gene using these cleavage sites.

BRIEF DESCRIPTION OF THE DRAWINGS

In the accompanying drawings, forming a part of the specification.

DESCRIPTION OF THE INVENTION

In accordance with the present invention, plasmid vectors are constructed in the following manner.

Figure 1:
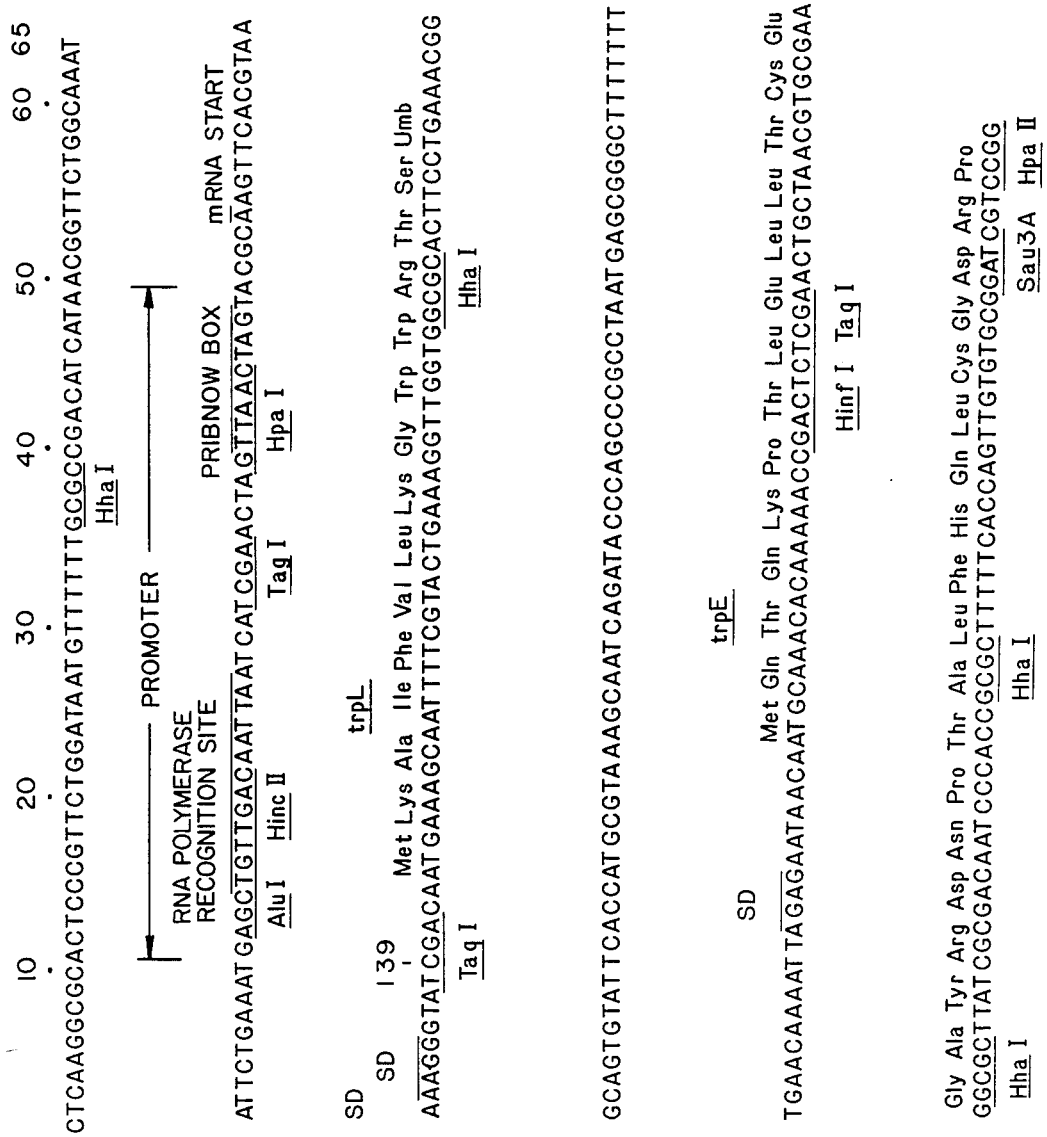
FIG. 1 illustrates the DNA base sequence around the tryptophan promoter and the SD sequence.
Figure 2:
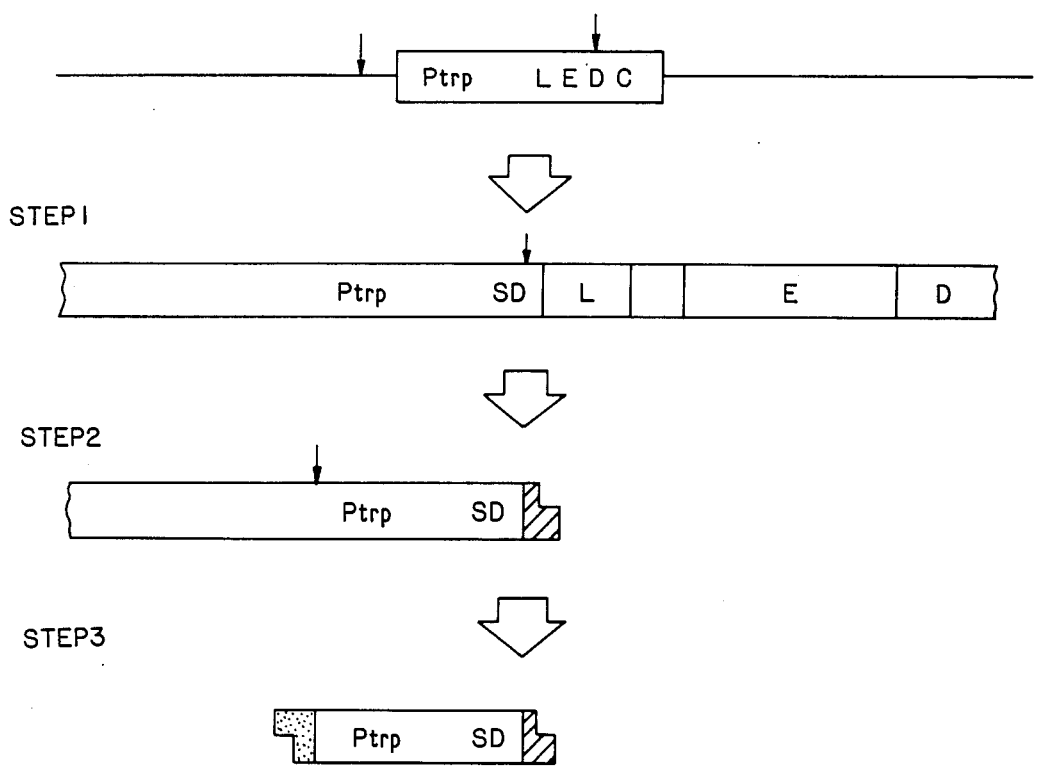
FIG. 2 is a flow chart illustrating construction of the trp portable promoter.

The plasmid vector containing the trp promoter is prepared by cloning a DNA fragment containing the promoter and SD sequence illustrated in FIG. 1, for example, the DNA fragment from the 1st to 139th base pairs in FIG. 1 into a vector such as pBR322, pBR325, pGA22, pACYC184 and pACYC177. The DNA sequence of the trp promoter region as is illustrated in FIG. 1, has been determined and is reported in G. N. Bennett et al.: J. Mol. Biol. 121, 113–137 (1978) and F. Lee et al.: J. Mol. Biol. 121, 193–217 (1978). Transducing phage (referred to as λptrp hereinafter) carrying a tryptophan operon is used as a source of DNA containing a trp promoter. Since it is difficult to cut out only the DNA fragment containing the promoter and SD sequence illustrated in FIG. 1 from the λptrp DNA using a restriction endonuclease, the plasmid vector having the trp promoter is constructed through the three steps shown in FIG. 2. The general method for constructing the plasmid vector is described by the following steps (a) to (d).

(a) Purification of λptrp DNA:

A microorganism of *Escherichia coli* wherein λptrp is lysogenized is cultured and the phages are purified from the lysate in a conventional manner to obtain λptrp DNAs after the induction of phages with Mitomycin C.

(b) Cloning of a trp promoter to a plasmid:

The λptrp DNA obtained as above is treated as follows to clone the trp operon.

Figure 10:
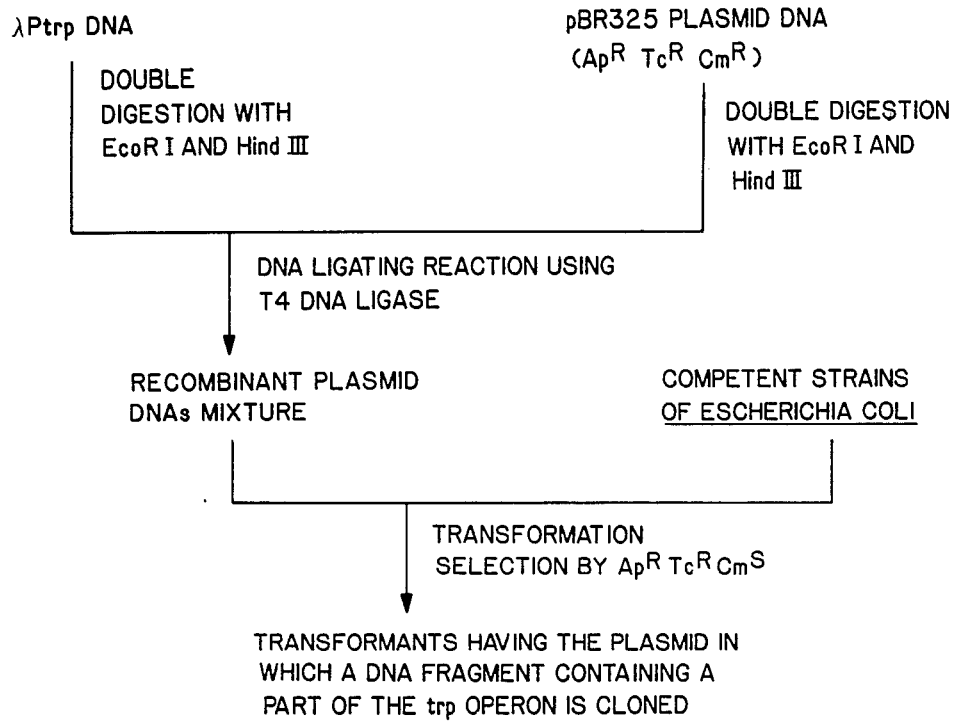
FIG. 10 is a flow chart illustrating the production of transformants having a plasmid containing part of the trp operon.

First transformants having a plasmid in which a DNA fragment containing a part of the trp operon is cloned are produced by the method shown in FIG. 10.

Figure 11:
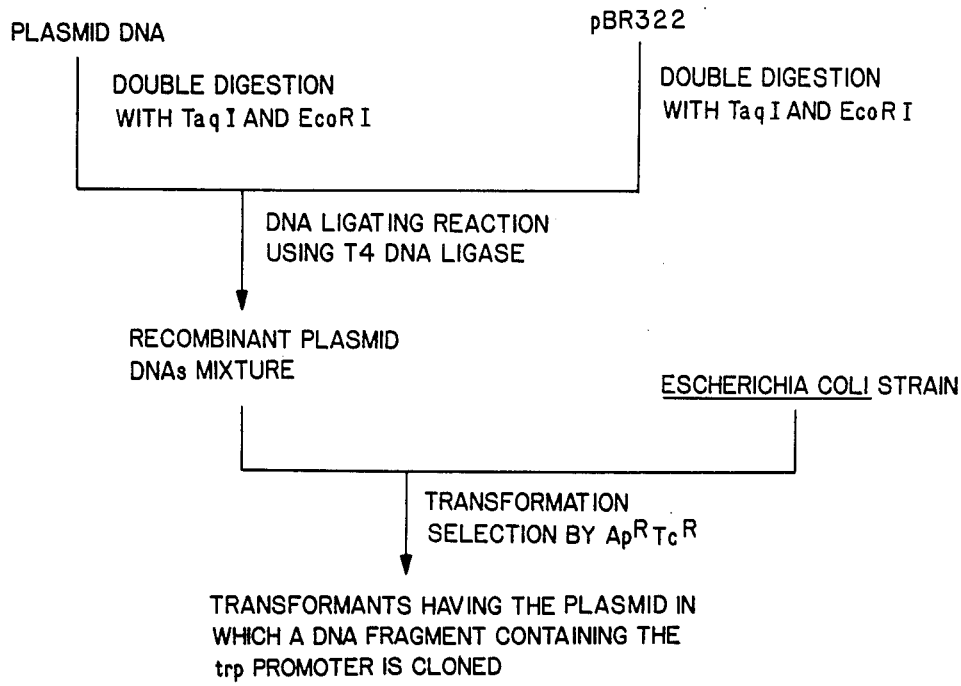
FIG. 11 is a flow chart illustrating the production of transformants having a plasmid containing the trp promoter.

Plasmid DNAs are isolated from the resultant transformants by conventional means and are then cloned in a vector and transformants are prepared by the method outlined in FIG. 11.

Figure 6:
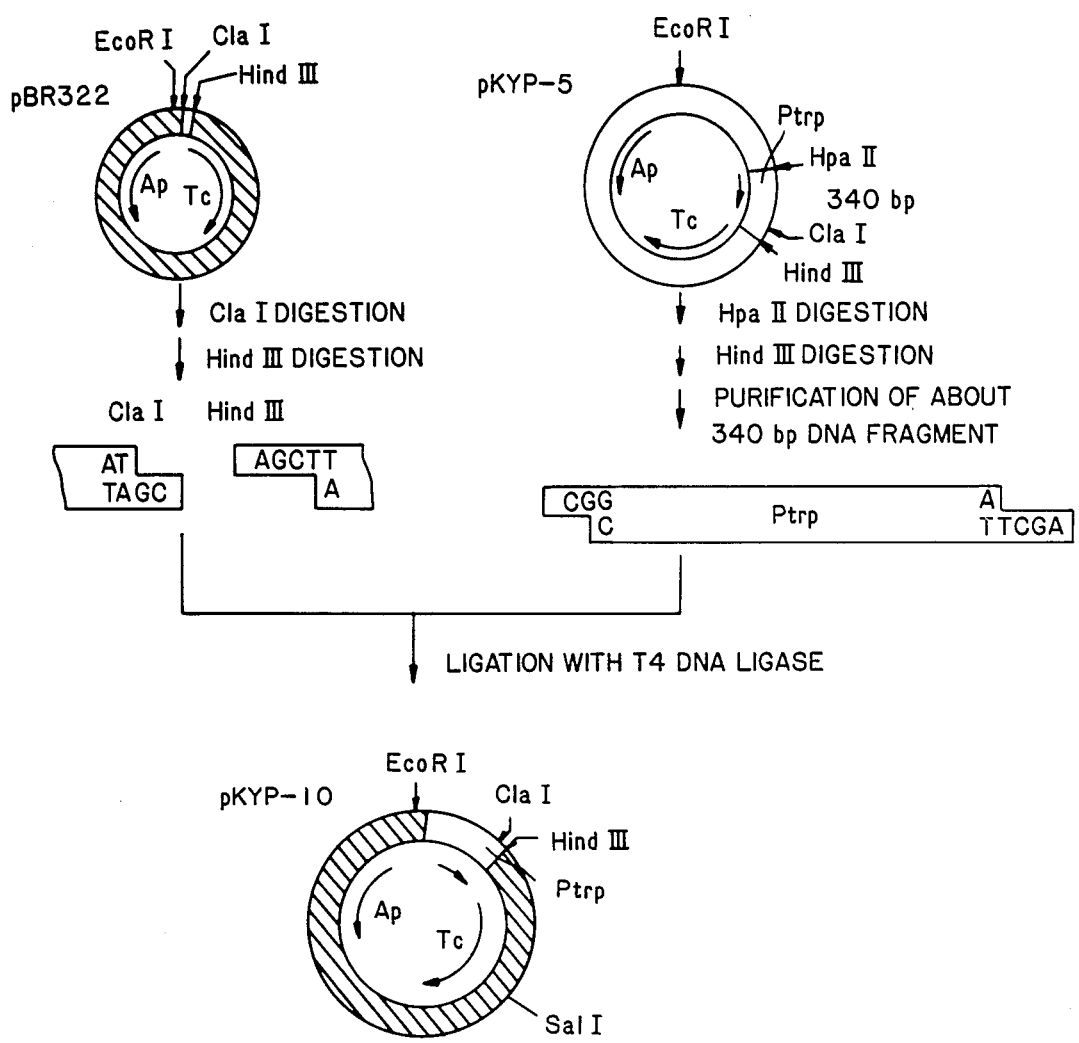
FIG. 6 is a flow chart illustrating construction of plasmid pKYP-10.

(c) Preparation of a portable promoter from the trp promoter:

A plasmid in which a DNA fragment containing the trp promoter is cloned is isolated from the transformant mentioned above and treated with a restriction endonuclease such as HpaII, HindIII and the like to shorten the plasmid as illustrated in FIG. 6.

(d) Connection of two or more trp promoters:

The plasmid is treated as illustrated in FIG. 7 to construct a plasmid having two or more trp promoters.

Examples of the plasmid vectors containing the trp promoter obtained by the foregoing procedure are: pKYP-1 wherein a 4.6 Kb DNA fragment derived from λtrpED is inserted into pBR325; pKYP-5 wherein a 2.6 Kb DNA fragment derived from pKYP-1 is inserted into pBR322; pKYP-10 wherein an about 370 bp DNA fragment derived from pKYP-5 is inserted into pBR322; pKYP-11 wherein an additional trp promoter is inserted into pKYP-10, yielding a total of two trp promoters; and pKYP-12 wherein an additional trp promoter is inserted into pKYP-11, yielding a total of three trp promoters.

The DNA coding for IFN-β is then inserted into the plasmid vector containing the trp promoter obtained as described above to prepare a recombinant plasmid wherein the IFN-β gene is inserted downstream from the trp promoter.

The gene coding for IFN-β has been cloned and the entire nucleotide sequence of the gene was determined by one of the present inventors, see T. Taniguchi et al.: Gene 10, 11–15 (1980). Furthermore, a recombinant, pTuIFNβ-5, has been constructed wherein the IFN-β gene is inserted downstream from the tufB promoter of *Escherichia coli* which produces 800 to 2,600 units/ml IFN-β in *Escherichia coli*. In the present invention, pTuIFNβ-5 is preferably used as a source of IFN-β gene, but other IFN-β genes prepared by other methods may be used. An *Escherichia coli* transformant carrying the plasmid pTuIFNβ-5 has been deposited with the American Type Culture Collection, U.S.A. under accession No. ATCC 31879.

Particularly preferred examples of the recombinant plasmids of the present invention are pLE-3 wherein the IFN-β gene is inserted into pKYP-12 and pLV-1, pLVX-1 and pMZ-2 which are derivatives of pLE-3.

Certain specific embodiments of the invention are illustrated by the following representative examples in which Examples 2 through 5 set forth specific processes for construction of the recombinant plasmids mentioned above.

EXAMPLE 1

Construction of a plasmid vector having a trp promoter:

(a) Purification of tryptophan transducing phage DNA:

A λptrp phage, λcI857trpED10 (referred to as λtrp ED hereinafter) G. F. Miozzari et al.: J. Bacteriol. 133, 1457 (1978) is lysogenized in *Escherichia coli* JA 194 strain (F−, λ−, r$_k$−, m$_k$−, Δtrp E5, leu6), J. Carbon et al.: Recombinant Molecules p. 355 (1977), Raven Press. The resultant lysogenic strain, JA 194 (λtrp ED) is cultured at 42° C. for 30 minutes to induce λtrp ED phages and prepare λphage lysate. The λphages are purified from the λphage lysate by the cesium chloride equillibrium density gradient centrifugation of Yamakawa et al.: "Chemicals of Nucleic Acids I" Tokyo Kagaku Dojin, p. 54–61, (1974). The λphages are further purified by phenol treatment and chloroform treatment according to the method of Yamakawa et al, supra, p. 62–65.

Figure 3:
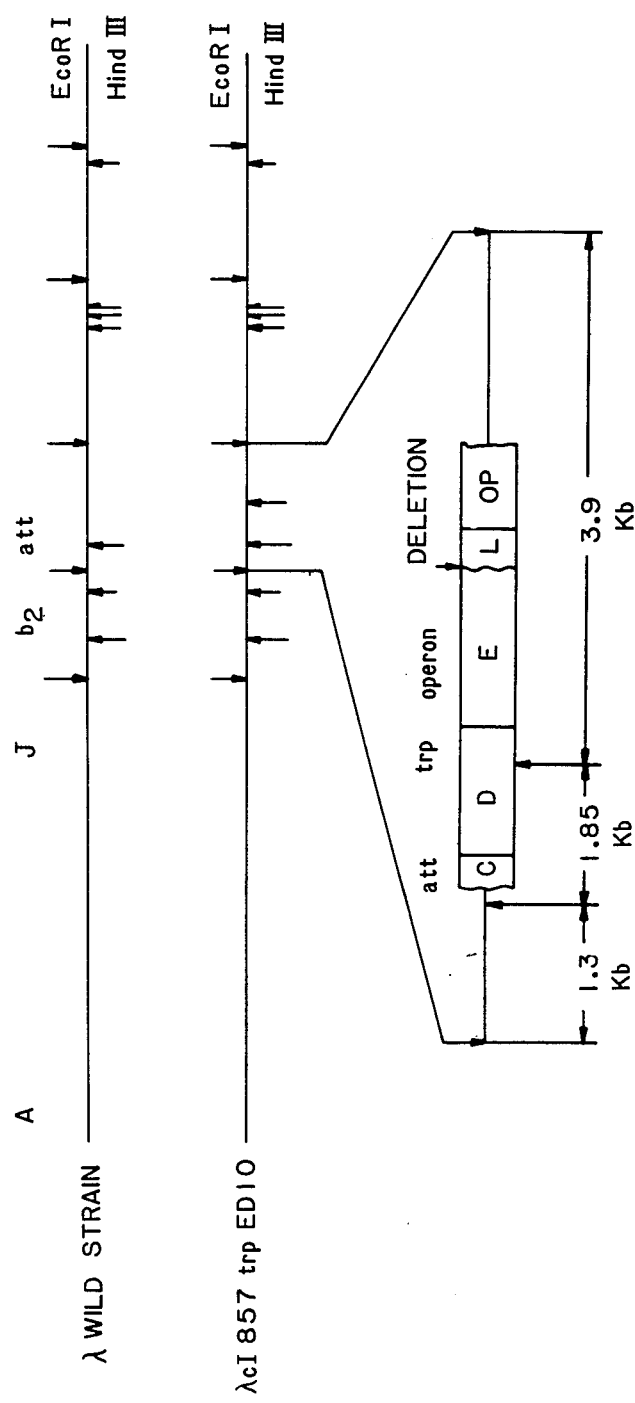
FIG. 3 illustrates the cleavage maps of the mild λ strain and λtrp ED phage DNA.
Figure 4A:
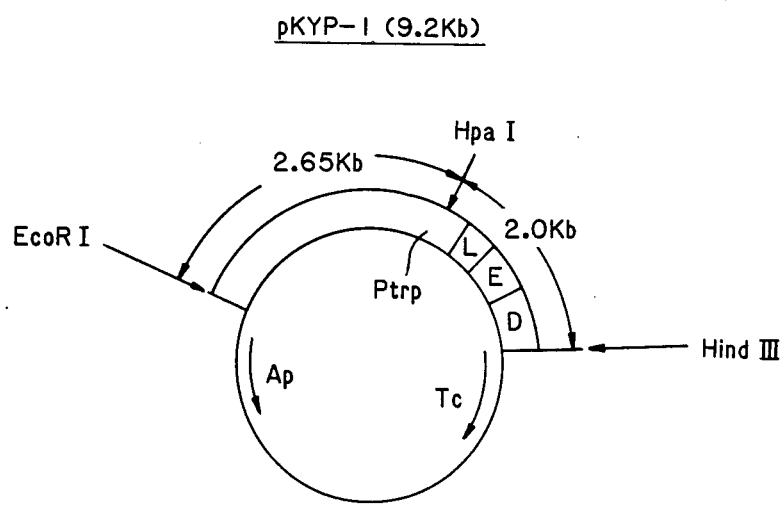
FIG. 4(A) illustrates the structure of the plasmid pKYP-1 and FIG. 4(B) illustrates that of the plasmid pKYP-5.

(b) Cloning of the trp promoter into a plasmid:

The cleavage map of the λtrp ED phage DNA purified as mentioned above for EcoRI and HindIII as illustrated in FIG. 3. Based on FIG. 3, cloning of the trp operon from λtrp ED phage DNA is carried out as follows. That is, 8 μg of λtrp ED DNA is digested at 37° C. for 2 hours with 16 units of EcoRI (product of Takara Shuzo Co., the same shall apply hereinafter) and 16 units of HindIII (product of Takara Shuzo Co., the same shall apply hereinafter) in 20 mM Tris-HCl (pH 7.5), 75 mM NaCl, 10 mM MgCl$_2$ and 5 mM dithiothreitol. Separately, 1 μg of plasmid pBR325 DNA is digested with 2 units of EcoRI and 2 units of HindIII by the same method as mentioned above (final volume: 30 μl). The reactions are stopped by heating at 65° C. for 5 minutes. Then, 15 μl each of the digests are mixed and 500 μM (final concentration) ATP and 5 units of T4 DNA ligase (product of New England Biolabs) are added. The mixture is allowed to react at 4° C. for 18 hours. *Escherichia coli* C600 SF strain, Cameron et al.: Proc. Natl. Acad. Sci. 72, 3416 (1975) is transformed with the plasmid mixture by the method of S. N. Cohen et al.: Proc. Natl. Acad. Sci. 69, 2110 (1972) and transformants which are resistant to ampicillin (Ap ®), resistant to tetracycline (Tc ®) and sensitive to chloramphenicol (Cm$^S$) are selected. Plasmid DNAs are isolated from the transformants of *Escherichia coli* and cleaved with EcoRI, HindIII and HpaI. One of the plasmid DNAs has the structure illustrated in FIG. 4(A) and is named pKYP-1.

Figure 4B:
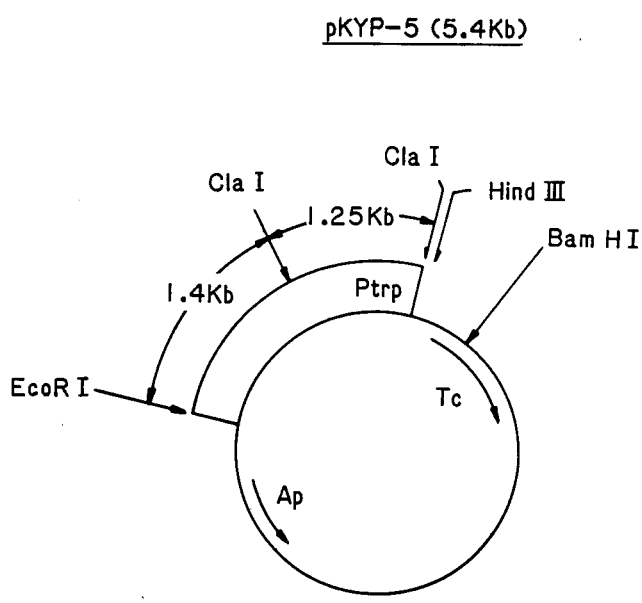
Figure 5:
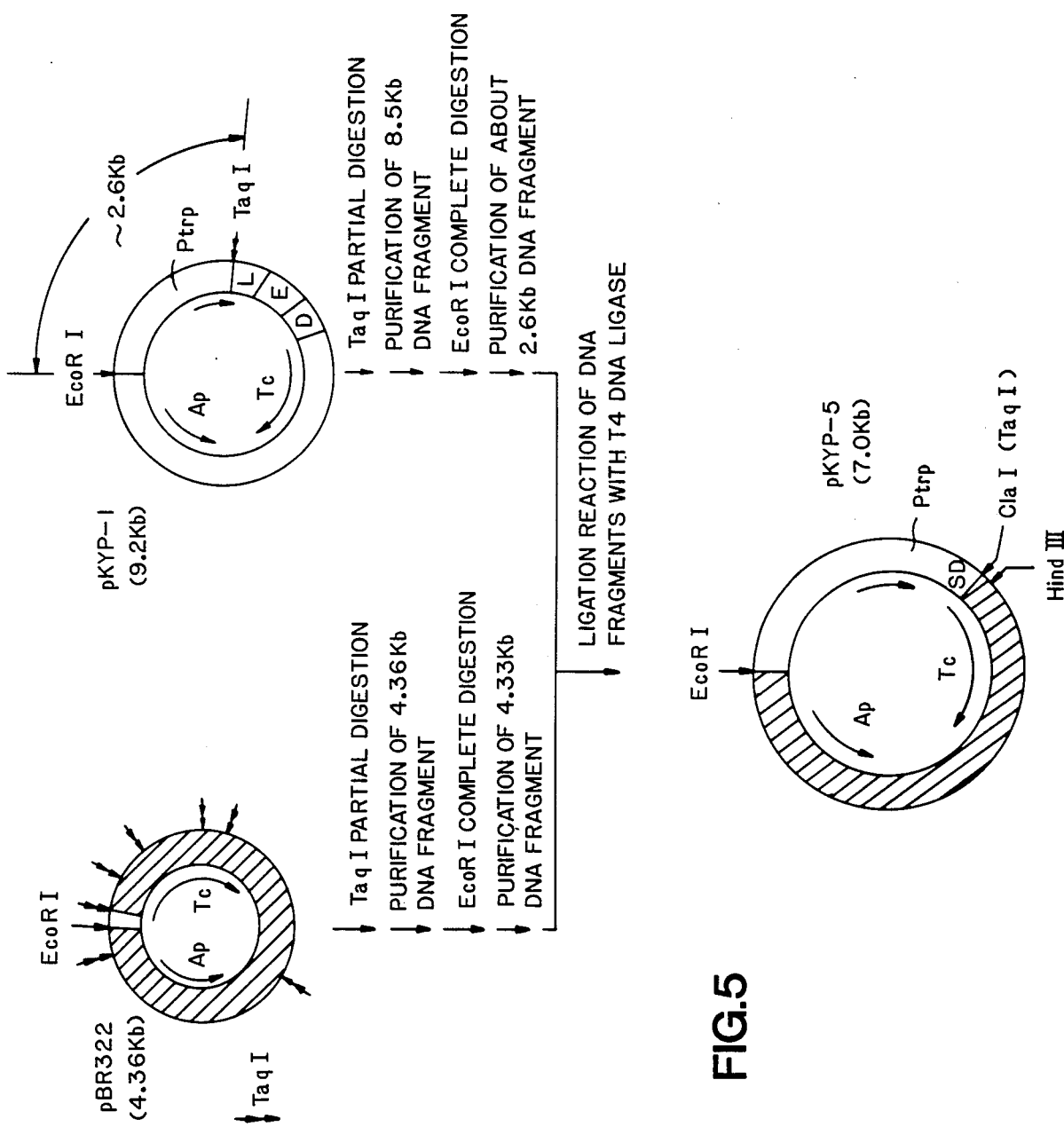
FIG. 5 is a flow chart illustrating construction of plasmid pKYP-5.

As illustrated in FIG. 1, a TaqI cleavage sits exists between 4 base pairs downstream from the SD sequence (AAGG) present downstream from the tryptophan promoter. The plasmid pKYP-1 is digested with TaqI and EcoRI and the digest is subjected to purification by agarose gel electrophoresis to obtain a 2.6 Kb (Kilobase) DNA fragment containing the tryptophan promoter and SD sequence. The 2.6 Kb DNA fragment is cloned in a known vector, pBR322, by the method as illustrated in FIG. 5. That is, 8 μg of pBR322 is digested at 45° C. for 60 minutes with 2 units of TaqI (product of Takara Shuzo Co.) in 100 μl of a reaction mixture comprising 10 mM Tris-HCl (pH 8.4), 6 mM MgCl$_2$, 100 mM NaCl and 6 mM 2-mercaptoethanol. After partial digestion with TaqI, the digest is subjected to low melting point agarose gel electrophoresis, Lars Wieslander: Analytical Biochemistry 98, 305 (1979), to obtain a 4.36 Kb purified DNA fragment. About 1.5 μg of the DNA fragment is completely digested at 37° C. for 3 hours with 3 units of EcoRI. About 1.0 μg of a 4.33 Kb DNA fragment is recovered by the same low melting point agarose gel electrophoresis as mentioned above. Then, 12 μg of pKYP-1 DNA is partially digested with 3 units of TaqI, about 2 μg of the resultant 8.5 Kb DNA fragment is purified by low melting point agarose gel electrophoresis and the DNA is completely digested with EcoRI by the same procedure as above to obtain about 0.5 μg of a purified 2.6 Kb DNA fragment. Then, 0.4 μg of the thus obtained 4.33 Kb DNA of pBR322 and 0.25 μg of the 2.6 Kb DNA fragment of pKYP-1 are added to 20 μl of a reaction solution consisting of 20 mM Tris-HCl (pH 7.6), 10 mM MgCl$_2$ and 10 mM dithiothreitol. Then, 0.5 mM ATP and 4 units of T4 DNA ligase are added to the mixture and reaction is carried out at 4° C. for 18 hours. *Escherichia coli* C600 SF8 strain is transformed with the plasmid DNA obtained as above. The plasmids in the transformant having Ap ® and Tc ® are isolated. The plasmid DNA is digested with 6 restriction endonucleases, EcoRI, HindIII, ClaI (product of Boehringer Mannheim GmbH), HpaI (product of Takara Shuzo Co.), HincII (product of Takara Shuzo Co.) and BamHI (product of Takara Shuzo Co.) to analyze the structure of the plasmid. The plasmid is recognized to have the structure illustrated in FIG. 4(B) and is named pKYP-5.

(c) Preparation of a portable promoter from the trp promoter:

The plasmid vector pKYP-5 mentioned above is applicable as a DNA introducing vector since it has a ClaI site and a HindIII site on the DNA of 1 to 20 base pairs downstream from the SD sequence. Since another ClaI site is present in pKYP-5 DNA besides the ClaI site immediately after the SD sequence and the fragment with the trp promoter obtained by cutting pKYP-5 DNA with EcoRI and HindIII is a little too large, i.e. 2.65 Kb, pKYP-5 is improved by the process as illustrated in FIG. 6 to obtain a plasmid having a DNA fragment containing a shorter trytophan promoter. That is, pKYP-5 DNA is digested with HpaII and HindIII and the digest is purified to obtain a DNA fragment of about 340 bp. The fragment is inserted into the pBR322 digested with ClaI and HindIII as illustrated in FIG. 6 to obtain pKYP-10. The structure of pKYP-10 is determined by digestion with EcoRI, ClaI, HindIII and HpaI and agarose gel electrophoresis.

Figure 7A:
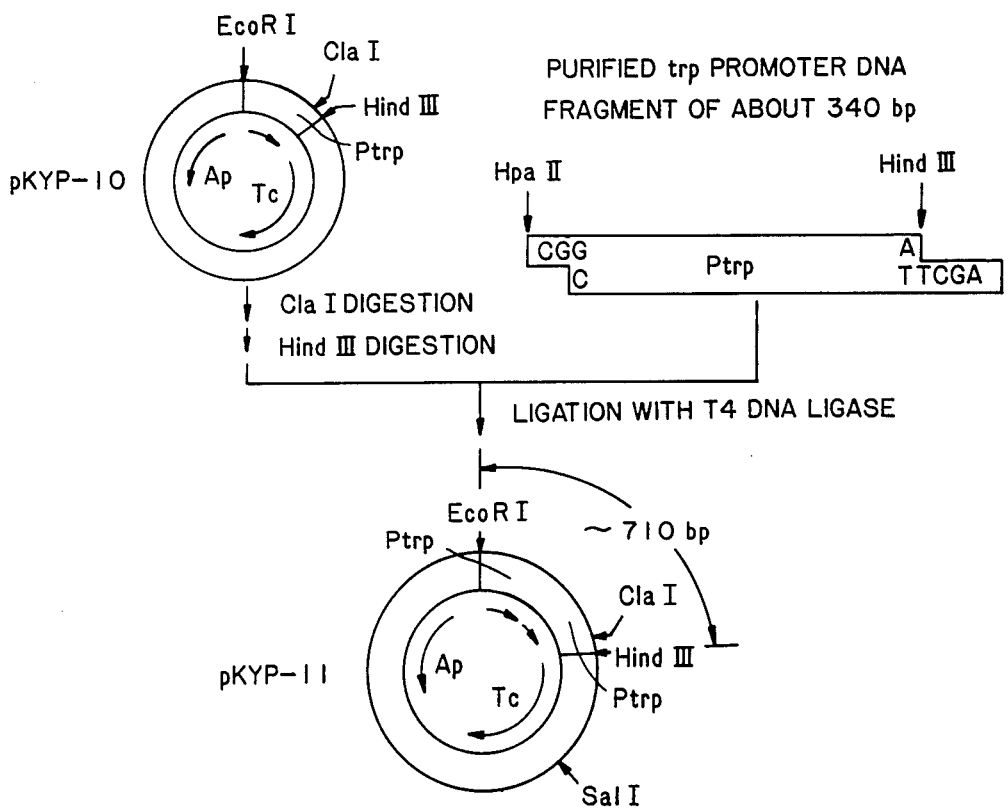
FIG. 7(A) is a flow chart illustrating construction of plasmid pKYP-11 and FIG. 7(B) illustrates the structure of plasmid pKYP-12.
Figure 7B:
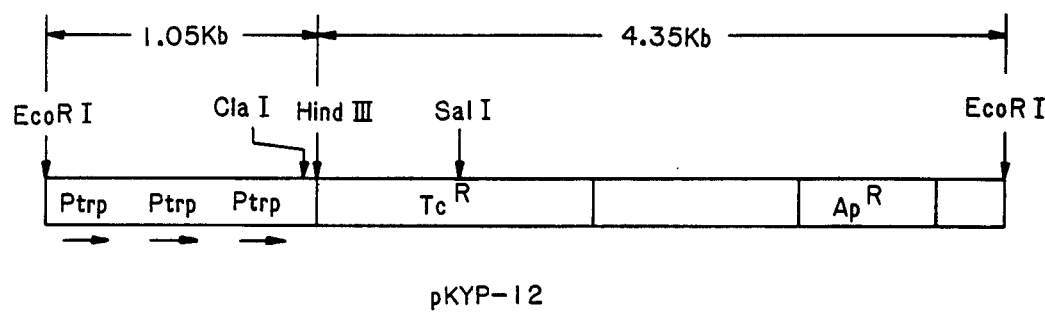

(d) Connection of two or more trp promoters:

In order to construct a plasmid vector having a stronger promoter activity, two trp promoters are inserted into the vector. That is, the DNA fragment of about 340 bp containing the trp promoter mentioned in step (c) above is inserted into the pKYP-10 digested with ClaI and HindIII to obtain pKYP-11 as illustrated in FIG. 7(A). The same procedure is repeated to construct pKYP-12 illustrated in FIG. 7(b) wherein three trp promoters are connected at the same orientation. The structure of pKYP-12 is confirmed by digestion with EcoRI, ClaI, HindIII and HpaI.

Plasmid vectors, pKYP-5, 10, 11 and 12 mentioned above are plasmid vectors wherein the DNA fragment containg the trp promoter is cloned in the plasmid pBR322. Other plasmids, such as pBR325, may also be employed for the construction of similar DNA introducing vectors. Analogous derivatives of pKYP-5, 10, 11 and 12 can be constructed by deleting the ampicillin-resistant gene or tetracycline-resistant gene or introducing other drug-resistant genes such as kanamycin-resistant gene, chloramphenicol-resistant gene and the like.

EXAMPLE 2

Figure 8:
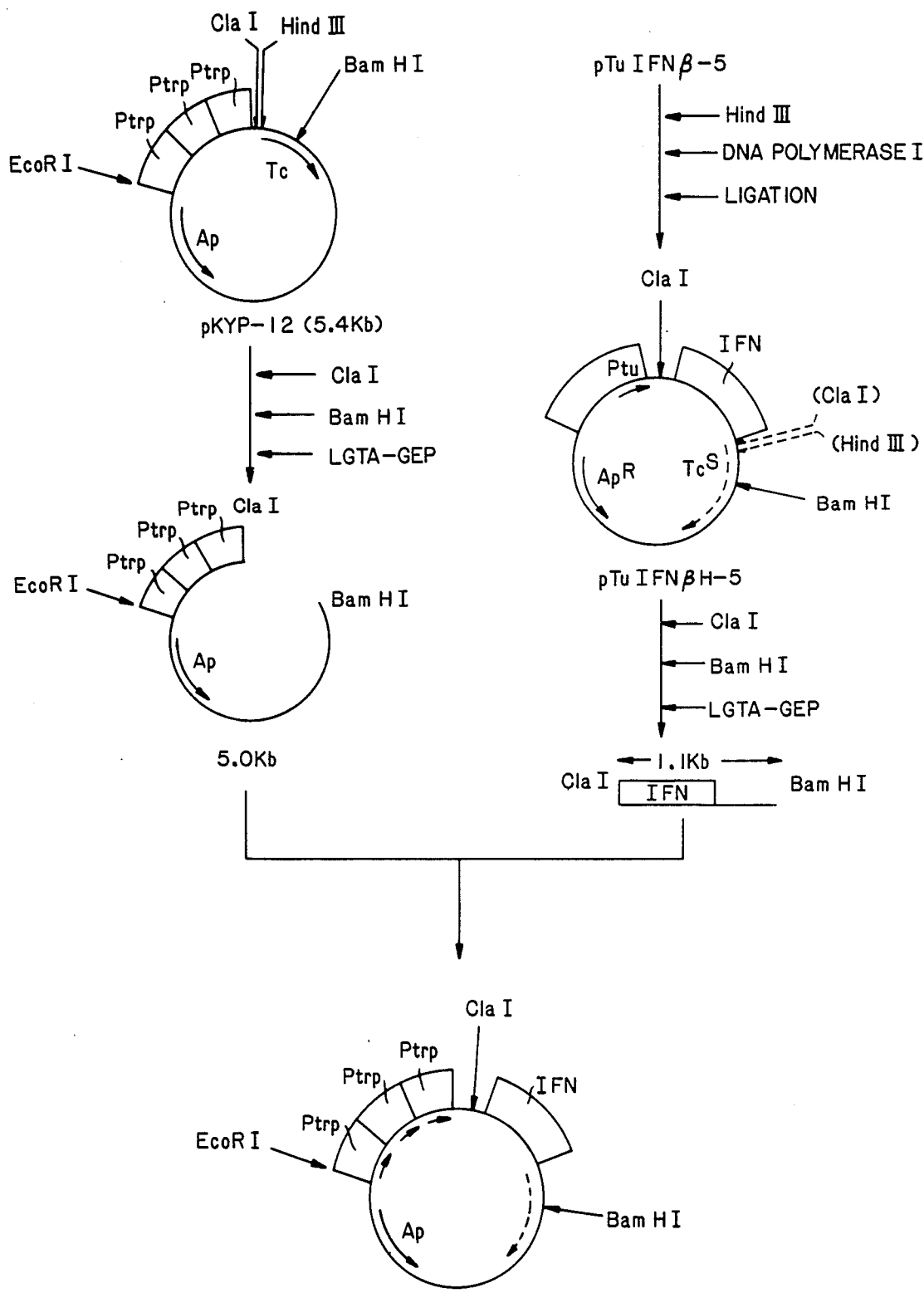
FIG. 8 is a flow chart illustrating construction of the recombinant plasmid pLE-3 containing IFN-β gene.

Insertion of the DNA coding for IFN-β into the plasmid vector pKYP-12:

Plasmid pTuIFNβ-5, isolated from ATCC 31879, by conventional techniques, is digested with HindIII. The digest is treated with DNA polymerase I (product of New England Biolabs) and subjected to ligation to obtain pTuIFNβH-5 illustrated in FIG. 8. The IFN-β gene recovered from pTuIFNβH-5 is then cloned in the plasmid pKYP-12 having a trp promoter. That is, 2 μg of pKYP-12 DNA is digested with 4 units of ClaI in 30 μl of a buffer solution (referred to as Cla⁻ buffer hereinafter) consisting of 10 mM Tris-HCl (pH 7.5), 6 mM MgCl$_2$ and 5 mM dithiothreitol at 37° C. for 2 hours. NaCl is added to a final concentration of 100 mM and the reaction is continued at 37° C. for 2 hours. The mixture is heated at 65° C. for 5 minutes to inactivate the enzyme and is then subjected to low melting point agarose gel electrophoresis to obtain 1.2 μg of a purified DNA of about 5 Kb containing the trp promoter. Separately, 15 μg of pTuIFNβH-5 DNA is digested with ClaI and BamHI and purified by low melting point agarose gel electrophoresis as described above to obtain about 1 μg of a DNA fragment (1.1 Kb) containing the IFN-β gene. The two DNA fragments obtained as above and illustrated as 5 Kb and 1.1 Kb in FIG. 8 are dissolved in a mixture of 20 mM Tris-HCl (pH 7.5), 6 mM MgCl$_2$, 5 mM dithiothreitol and 500 μM ATP. 4 units of T4 DNA ligase is added and the mixture is allowed to react at 4° C. for 18 hours. *Escherichia coli* HB101 is transformed with the mixture of the thus obtained recombinants by conventional technique to obtain colonies resistant to ampicillin. Plasmids are recovered from the culture of the colonies. One of the plasmids is pLE-3 illustrated in FIG. 8. The structure of pLE-3 is confirmed by agarose gel electrophoresis after the digestion of DNA with ClaI, EcoRI, HindIII and BamHI. It is confirmed by the method of Maxam & Gilbert, Proc. Natl. Acad. Sci. 74, 560 (1977) that the base sequence from the SD sequence, AAGG, to the initiation codon, ATG, in the plasmid pLE-3 is "AAGG GTATCGATG".

*Escherichia coli* containing plasmid pLE-3 has been deposited with the American Type Culture Collection, U.S.A. as *Escherichia coli* ILE-3, ATCC 39010.

EXAMPLE 3

Figure 9:
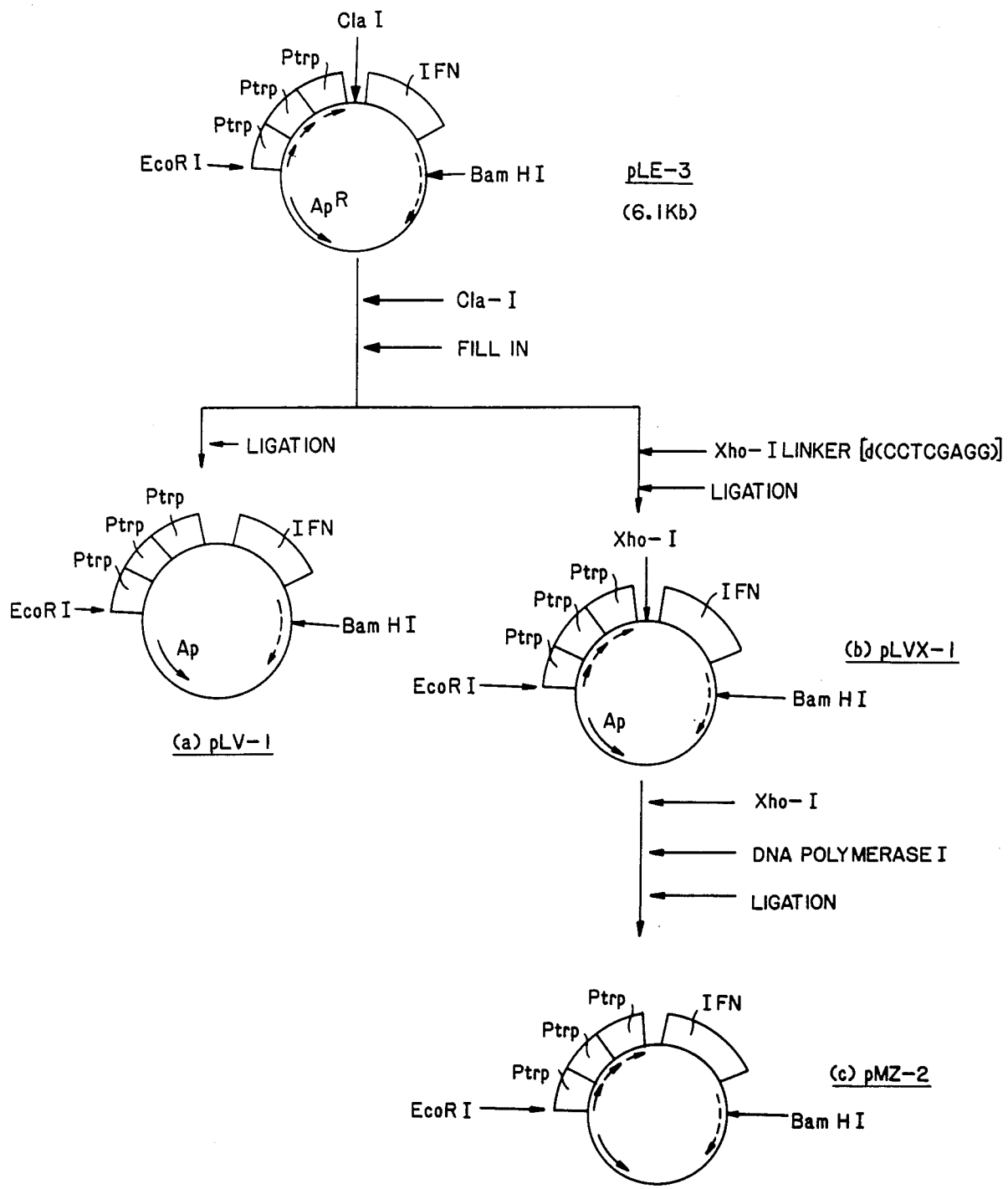
FIG. 9 is a flow chart illustrating construction of the recombinant plasmids pLV-1, pLVX-1 and pMZ-2 containing IFN-β gene.

In this example, 2 μg of the pLE-3 DNA obtained in Example 2 is dissolved in 30 μl of the Cla⁻ buffer and 4 units of ClaI is added. The mixture is allowed to react at 37° C. for 2 hours and is then heated at 65° C. for 5 minutes to inactivate ClaI. Then, d-GTP and d-CTP are added to a concentration of 20 μM each and 6 units of *Escherichia coli* DNA polymerase I (1 μl) is added. The mixture is allowed to react at 15° C. for 1 hour. Then, 5 mM dithiothreitol, 500 μM ATP and 20 units of T4 DNA ligase are added. The mixture is allowed to react at 4° C. for 18 hours. *Escherichia coli* HB101 is transformed using the reaction mixture in a conventional manner to obtain an Ap ® colony. A plasmid is recovered from the culture of the colony, named pLV-1, is illustrated in FIG. 9(a). The structure of pLV-1 is confirmed by agarose gel electrophoresis after the digestion of DNA with EcoRI, ClaI, HindIII and BamHI. It is confirmed by the method of Maxam & Gilbert that the base sequence from the SD sequence to the initiation codon (ATG) in pLV-1 is "AAGGGTATCG-CGATG". *Escherichia coli* containing plasmid pLV-1 has been deposited with the American Type Culture Collection, U.S.A. as *Escherichia coli* ILV-1, ATCC 39025.

EXAMPLE 4

Plasmid pLVX-1 is obtained from pLE-3 mentioned in Example 2 as follows. First, 3 μg of pLE-3 DNA is dissolved in 40 μl of the Cla-buffer and 6 units of ClaI is added. The mixture is allowed to react at 37° C. for 2 hours and heated at 65° C. for 5 minutes to inactivate CaII. Then, d-GTP and d-CTP are added to a concentration of 20 μM each and 6 units of *Escherichia coli* DNA polymerase I is added. The mixture is allowed to react at 15° C. for 1 hour. Then, 5 mM dithiothreitol, 500 μM ATP, 0.1 μg of Xho-Linker, d(CCTCGAGG), (product of Colaborative Res.) and 20 units of T4 DNA ligase are added and ligation is carried out at 4° C. for 18 hours. *Escherichia coli* HB101 is transformed using the recombinant plasmid mixture by conventional technique to obtain an Ap ® colony. A plasmid is recovered from the culture of the colony, named pLVX-1, is illustrated in FIG. 9(b). The structure of pLVX-1 is confirmed by agarose gel electrophoresis after the digestion of DNA with EcoRI, Xho-I, HindIII and BamHI. It is confirmed by the method of Maxam & Gilbert that the base sequence from the SD sequence to the initiation codon (ATG) in pLVX-1 is "AAGGGTATCGCCT-CGAGGCGATG." *Escherichia coli* containing plasmid pLVX-1 has been deposited with the American Type Culture Collection, U.S.A. as *Escherichia coli* ILVX-1, ATCC 39024.

EXAMPLE 5

Plasmid pMZ-2 is derived from pLVX-1 obtained in Example 4 by adjusting the length from the SD sequence to the initiation condon as illustrated in FIG. 9(c). That is, 5 μg of pLVX-1 is dissolved in 50 μl of the Cla-buffer and 150 mM NaCl and 10 units of XhoI are added. The mixture is allowed to react at 37° C. for 2 hours and is then heated at 65° C. for 5 minutes to inactivate XhoI. Then, 8 units of DNA polymerase I is added and the mixture is allowed to react at 37° C. for 30 minutes to remove the cohesive end formed by the digestion with XhoI. After inactivating DNA polymerase by heating at 70° C. for 15 minutes, 5 mM dithiothreitol, 500 μM ATP and 30 units of T4 DNA ligase are added and the ligation reaction is carried out. *Escherichia coli* HB101 is transformed with the DNA solution obtained above to obtain an Ap ® colony. A plasmid is recovered from the culture of the colony, named pMZ-2, is illustrated in FIG. 9(c). The structure of pMZ-2 is confirmed by agarose gel electrophoresis after the digestion of DNA with EcoRI, HindIII, XhoI and BamHI.

*Escherichia coli* containing plasmid pMZ-2 has been deposited with the American Type Culture Collection, U.S.A. as *Escherichia coli* IMZ-2, ATCC 39023.

EXAMPLE 6

Productivity of interferon by *Escherichia coli* HB101 strains having the recombinant plasmids pLE-3, pLV-1, pLVX-1 and pMZ-2 obtained in Examples 2 to 5, that is ILE-3, ILV-1 and IMZ-2, respectively is examined as follows. ILE-3, ILV-1, ILVX-1 and IMZ-2 are cultured at 37° C. for 18 hours in a LG medium (pH adjusted to 7.0 with NaOH) consisting of 10 g/l trypton, 5 g/l yeast extract 5 g/l NaCl and 2 g/l glucose. Then, 0.2 ml of the culture is inoculated in 10 ml of an MCG medium (pH 7.2) consisting of 0.6% $Na_2HPO_4$, 0.3% $KH_2PO_4$, 0.5% NaCl, 0.1% $NH_4Cl$, 0.5% glucose, 0.5% casamino acid, 1 mM $MgSO_4$ and 4 μg/ml vitamin $B_1$. Culturing is carried out at 30° C. for 4 to 8 hours. Then, 10 μg/ml indolacrylic acid (referred to as IAA hereinafter) which is an inducer of the trytophan gene is added and culturing is continued for an additional 5 to 12 hours. Cells are harvested by centrifugation at 8000 rpm for 10 minutes and washed with 30 mM NaCl and 30 mM Tris-HCl (pH 7.5) buffer solution. The washed cells are suspended in 1 ml of the buffer solution mentioned above and 200 μg of lysozyme and 5 μl of 0.25M EDTA (ethylene diamine tetraacetic acid) are added. The mixture is allowed to stand at 0° C. for 30 minutes. Freezing and melting are repeated three times to disrupt the cells. The disrupted cells are subjected to centrifugation at 15,000 rpm for 30 minutes to obtain a supernatant fluid. The amount of the interferon in supernatant is determined by the method of J. A. Armstrong et al.: Appl. Microbiol. 21, 723–725 (1971), wherein Versicular Stomatitis Virus is used as a virus and Wish cell derived from human amnion cells is used as an animal cell.

The result is shown in Table 1.

TABLE 1

| Strain | Plasmid contained | β-IFN (units/l) |
|---|---|---|
| ILE - 3 | pLE - 3 | $2 \times 10^8 - 6 \times 10^8$ |
| ILV - 1 | pLV - 1 | $7 \times 10^8 - 5 \times 10^9$ |
| ILVX - 1 | pLVX - 1 | $5 \times 10^6 - 2 \times 10^7$ |
| IMZ - 2 | pMZ - 2 | $1 \times 10^9 - 8 \times 10^9$ |

What is claimed is:

1. A recombinant plasmid wherein a DNA fragment coding for human interferon-β is inserted downstream from at least one tryptophan promoter, said plasmid being selected from the group consisting of plasmids pLE-3, pLV-1 and pMZ-2.

* * * * *

UNITED STATES PATENT AND TRADEMARK OFFICE
CERTIFICATE OF CORRECTION

PATENT NO. : 4,686,191

DATED : August 11, 1987

INVENTOR(S) : SEIGA ITOH, ET AL.

It is certified that error appears in the above-identified patent and that said Letters Patent is hereby corrected as shown below:

Cover Page, at [73] Assignees: "Hakko Kogyo Co., Ltd. Kyowa;" should read: --Kyowa Hakko Kogyo Co., Ltd.--.

Cover Page, at [30], Foreign Application Priority Data: "Dec. 25, 1981 [JP] Japan ..... 56-21393" should read: --Dec. 25, 1981 [JP] Japan ..... 56-213193--.

Cover Page, at [56] References Cited, under "OTHER PUBLICATIONS", "M. Houghton, et al.", "51-57" should read --51-67--.

Cover Page, at [56] References Cited, under "OTHER PUBLICATIONS", "H. Shepard, et al.,", "Bindiny" should read --Binding--.

Column 4, line 47, "(Ap®)" should read --$(Ap^R)$--.

line 48, "(Tc®)" should read --$(Tc^R)$--.

Column 5, line 22, "Ap®" should read --$Ap^R$--.

line 23, "Tc®" should read --$Tc^R$--.

Column 6, line 65, "Ap®" should read --$Ap^R$--.

Column 7, line 25, "Ap®" should read --$Ap^R$--.

line 54, "Ap®" should read --$Ap^R$--.

UNITED STATES PATENT AND TRADEMARK OFFICE
CERTIFICATE OF CORRECTION

PATENT NO. : 4,686,191

DATED : August 11, 1987

INVENTOR(S) : SEIGA ITOH, ET AL.

It is certified that error appears in the above-identified patent and that said Letters Patent is hereby corrected as shown below:

Column 8, line 12, "ILV-1 and" should read:
   --ILV-1, ILVX-1 and--.

Signed and Sealed this

Eighth Day of December, 1987

Attest:

DONALD J. QUIGG

Attesting Officer

Commissioner of Patents and Trademarks